United States Patent
Nakajima et al.

(10) Patent No.: US 7,381,837 B2
(45) Date of Patent: Jun. 3, 2008

(54) METHOD AND APPARATUS FOR CONTROLLING FEED OF GASEOUS REACTION COMPONENT

(75) Inventors: Hidehiko Nakajima, Himeji (JP); Yoshiyuki Harano, Hyogo (JP); Manabu Yamada, Himeji (JP)

(73) Assignee: Daicel Chemical Industries, Ltd., Osaka-Shi (JP)

( * ) Notice: Subject to any disclaimer, the term of this patent is extended or adjusted under 35 U.S.C. 154(b) by 408 days.

(21) Appl. No.: 10/503,303

(22) PCT Filed: Feb. 26, 2003

(86) PCT No.: PCT/JP03/02105

§ 371 (c)(1),
(2), (4) Date: Aug. 3, 2004

(87) PCT Pub. No.: WO03/072236

PCT Pub. Date: Sep. 4, 2003

(65) Prior Publication Data

US 2005/0154228 A1    Jul. 14, 2005

(30) Foreign Application Priority Data

Feb. 27, 2002    (JP)    ............... 2002-051797

(51) Int. Cl.
*C07C 51/12* (2006.01)
*C07C 51/14* (2006.01)

(52) U.S. Cl. ...................... 562/519; 562/521

(58) Field of Classification Search ............. 429/22, 429/25, 19; 422/105; 562/517, 519, 607
See application file for complete search history.

(56) References Cited

U.S. PATENT DOCUMENTS 3,563,887 A    2/1971    Fraser et al.

(Continued)

FOREIGN PATENT DOCUMENTS

EP    0 124 333 A2    11/1984

(Continued)

*Primary Examiner*—Karl Puttlitz
(74) *Attorney, Agent, or Firm*—Birch, Stewart, Kolasch & Birch, LLP

(57) ABSTRACT

A method comprises continuously supplying an alcohol to a pressurized reaction system, pressurizing carbon monoxide with a compressor 8 attached to a first feed line 22, for continuously supplying carbon monoxide to the reaction system via a second feed line 23 with a reference flow rate F, and converging excess carbon monoxide in the reaction system in the first feed line via a branched circulation line 24 for allowing to react alcohol with carbon monoxide. The reference flow rate F in the second feed line 23 is a total rate of a reference consumption flow rate Fcs in the reaction and a flow rate F1 in excess rate over a fluctuation consumption flow rate $\Delta$Fcv in the reaction system (F=Fcs+F1, F1>$\Delta$Fcv). According to the pressure fluctuation of the gaseous phase in the reaction system, the flow rate in the circulation line 24 is controlled to a flow rate Fr=F1−$\Delta$Fcv and the feed flow rate in the first feed line 22 is controlled to a flow rate Fsu=Fcs+$\Delta$Fcv, for compensating a consumption rate variation in the reaction system with the feed flow rate of carbon monoxide. This ensures discharge inhibition of the gaseous reactant in a liquid phase pressurized reaction system (such as carbonylation reaction system) and effective utilization of the reactant for the reaction.

7 Claims, 3 Drawing Sheets

U.S. PATENT DOCUMENTS

| | | | |
|---|---|---|---|
| 6,255,527 B1 * | 7/2001 | Muskett | 562/519 |
| 2001/0024746 A1 * | 9/2001 | Ueda et al. | 429/22 |

FOREIGN PATENT DOCUMENTS

| | | |
|---|---|---|
| EP | 0 573 920 A2 | 12/1993 |
| EP | 0 983 792 A1 | 3/2000 |
| EP | 1 364 937 A1 | 11/2003 |
| JP | 48-54011 A | 7/1973 |
| JP | 56-81536 A | 7/1981 |
| JP | 6-321847 A | 11/1994 |
| JP | 10-508594 A | 8/1998 |
| JP | 2000-25723 A | 4/2000 |
| WO | WO 96/14287 A1 | 5/1996 |
| WO | WO-99/65097 A1 | 12/1999 |
| WO | WO-01/92147 A1 | 12/2001 |

* cited by examiner

METHOD AND APPARATUS FOR CONTROLLING FEED OF GASEOUS REACTION COMPONENT

TECHNICAL FIELD

This invention relates to a feed controlling method of a gaseous reactant and a feed apparatus (or control apparatus) thereof which are useful for effectively utilizing the gaseous reactant for a carbonylation reaction or other reactions.

BACKGROUND ART

Carboxylic acids (e.g., acetic acid) or derivatives thereof (e.g., methyl methacrylate) have been produced industrially by use of carbonylation reactions. For example, Japanese Patent Application Laid-Open No. 54011/1973 (JP-48-54011A) discloses a carbonylation method in which an olefin, an alcohol or an ester thereof, a halide, or an ether derivative is allowed to react in a liquid phase with carbon monoxide in the presence of a catalytic system containing a rhodium or iridium component and an iodine or bromine component. In this process, at least a part of a liquid reaction product is supplied, without heating, to a separation zone which is substantially low in pressure to vaporize or evaporate at least a part of the above-mentioned carbonylation product, the vaporized carbonylation product is taken out, and the residual liquid reaction product is recirculated to the above-mentioned reaction zone. This document describes the removal of unreacted carbon monoxide from the reactor. Japanese Patent Application Laid-Open No. 321847/1994 (JP-6-321847A) discloses a carbonylation product recovering method for maintaining the concentration of water in the liquid component at least at 0.5 weight % in which an iridium catalyst is used as a carbonylation catalyst, wherein a vapor component containing the carbonylation product and a liquid component containing the iridium catalyst are produced by vaporization of the reaction product and the vapor component is separated from the liquid component. This document illustrates the discharge of unreacted carbon monoxide as exhaust gas from the reactor.

Japanese Patent Application Laid-Open No. 508594/1998 (JP-10-508594A) proposes a method comprising the steps of producing a carboxylic acid in a first region by liquid phase carbonylation in the presence of a rhodium catalyst, partially vaporizing the reaction mixture in a second region, purifying a vapor fraction containing the produced carboxylic acid and recycling the non-vaporized liquid fraction containing the catalyst to the first region, wherein carbon monoxide is supplied to the non-vaporized liquid fraction produced from the second region by avoiding the return of carbon monoxide to the second region in order to prevent the loss of carbon monoxide.

Japanese Patent Application Laid-Open No. 95723/2000 (JP-2000-95723A) discloses a control method for a process of producing acetic acid by carbonylation, wherein the flow of carbon monoxide passing through a control valve is measured, the average value of the carbon monoxide flow per a predetermined time is calculated, a fixed value is added to this average carbon monoxide flow to calculate the maximum flow rate of carbon monoxide, and the operation is performed so that the flow rate of carbon monoxide into the reactor does not exceed the maximum flow rate.

However, these carbonylation methods are pressurized reaction systems in which the reaction is carried out by pressurizing carbon monoxide with a compressor. In order to inhibit the occurrence of surging in such pressurized reaction systems, carbon monoxide is supplied to the reaction system with maintaining a constant pressure and a constant flow rate at the inlet and the outlet of the compressor. Meanwhile, the pressurized reaction system, in which the reaction is carried out under a predetermined applied pressure, causes fluctuation or variation of the consumption rate of carbon monoxide with varying reaction temperatures. In particular, in an actual producing or manufacturing plant the consumption rate of carbon monoxide is significantly fluctuated even when the reaction temperature in the reaction system slightly varies. Accordingly, in order to prevent a pressure drop in the reaction system, carbon monoxide in an excess amount over the consumption rate of carbon monoxide at a steady state (reference consumption rate) is supplied to the reaction system, as a reference flow rate, from the outlet of the compressor on the assumption that the consumption rate is large. Therefore, in the case where the consumption rate of carbon monoxide is less than the reference consumption rate in the reaction system, an excess of carbon monoxide in the reaction system is emitted or discharged and burned at the outside of the reaction system as a flare for retaining the pressure of the reaction system at a given value, and ensuring a stable operation. However, in such a system it is impossible to utilize carbon monoxide effectively, resulting in a great economical loss.

Further, in a carbon monoxide-producing plant (carbon monoxide-manufacturing plant), and a producing plant (e.g., acetic acid-producing plant) in which the carbonylation reaction is conducted with carbon monoxide produced by the carbon monoxide-producing plant, each of the carbon monoxide feed system and the carbonylation reaction system (or reaction system including separation and purification) is independently controlled. It is therefore impossible to reflect fluctuation factors in the reaction system (such as a pressure fluctuation) when controlling the carbon monoxide-producing plant and the feed system. Thus, it is difficult to more efficiently reduce the emission or discharge of carbon monoxide and to effectively utilize carbon monoxide for the carbonylation reaction.

It is, therefore, an object of the present invention to provide a control method and a control apparatus in which the gaseous reactant (such as carbon monoxide) is effectively used for the reaction in the pressurized reaction system.

Another object of the present invention is to provide a control method and a control apparatus in which the emission (or discharge) of the gaseous reactant is inhibited or suppressed and which is useful for subjecting the gaseous reactant to a reaction with economical advantages.

It is still another object of the present invention to provide, in a pressurized reaction system (such as a carbonylation reaction system) in which an excess amount of the gaseous reactant over the reference flow rate is continuously supplied industrially, a control method and a control apparatus for utilizing the gaseous reactant effectively for a reaction even when the consumption rate of carbon monoxide varies in the reaction system.

DISCLOSURE OF THE INVENTION

The inventors of the present invention made intensive studies to achieve the above objects, and finally found that, in a pressurized reaction system (e.g., a carbonylation reaction system) in which the gaseous reactant supplied with a reference consumption flow rate (reference reaction consumption rate) Fcs at a steady state is consumed accompanied with a fluctuation flow rate $\Delta Fcv$, the emission or discharge of the gaseous reactant can be reduced to almost zero while maintaining the pressure at a feed line (and a reference flow rate F) constant even when the consumption rate of the gaseous reactant varies with fluctuation of the reaction temperature and other factors, by supplying the gaseous reactant to the reaction system through a feed line with the reference flow rate F having an excess of F1 over the reference consumption flow rate Fcs, circulating an excess amount of the gaseous reactant (F1–ΔFcv) to the feed line through (or via) a circulation line for compensating or absorbing a consumption rate fluctuation ΔFcv of the gaseous reactant in the reaction system by the feed rate (Fcs+ ΔFcv) of the gaseous reactant from the gas feed system to the feed line. The present invention was accomplished based on the above findings.

That is, the method of the present invention comprises continuously supplying a gaseous reactant from a gas feed system to a pressurized reaction system through a feed line, and circulating an excess amount of the gaseous reactant in the reaction system from the feed line to the reaction system via a circulation line, wherein based on (or in relation to) a pressure fluctuation of a gaseous phase in the reaction system, the feed flow rate (or a feed pressure) of the gaseous reactant from the gas feed system is controlled in connection with the circulation flow rate (return flow rate) of the gaseous reactant in the circulation line, and the gaseous reactant is supplied to the reaction system via the feed line with a predetermined reference flow rate. Moreover, the apparatus of the present invention comprises a feed line for supplying a gaseous reactant to a pressurized reaction system; a feed unit for supplying the gaseous reactant to the feed line; a pressurizing means, disposed at the feed line, for pressurizing the gaseous reactant from the feed unit; a circulation line for circulating an excess amount of a gaseous reactant in the reaction system to the reaction system; and a control unit for controlling the flow rate of the gaseous reactant in the circulation line and controlling the feed rate of the gaseous reactant from the feed unit to the feed line based on (or in relation to) a pressure fluctuation of a gaseous phase in the reaction system to supply the gaseous reactant to the reaction system via the feed line with a predetermined reference flow rate. Such a method and an apparatus ensure feeding of the gaseous reactant to the reaction system through the feed line with a predetermined flow rate by controlling the feed flow rate of the gaseous reactant in reference to the deviation of the circulation flow rate with respect to a reference flow rate in the circulation line.

In this method, the gaseous reactant converged in the feed line and the circulation line may be continuously supplied to the reaction system with a reference flow rate F which is defined as the total flow rate of a reference consumption flow rate Fcs in the reaction system and an excess flow rate F1 in an excess amount over the fluctuation consumption flow rate ΔFcv in the reaction system. Moreover, the gaseous reactant may be fed to the reaction system with the reference flow rate F by compensating or absorbing the consumption rate fluctuation of the gaseous reactant in the reaction system with a feed rate of the gaseous reactant from the gas feed system. The gas feed source of the gas feed system may be in a liquid form (or a liquefied gaseous reactant).

Further, according to the method or apparatus of the present invention, the flow rate of the gaseous reactant in the feed line may be controlled to the reference flow rate based on at least the pressure fluctuation of the gaseous phase in the reaction system. For example, the pressure fluctuation of the gaseous phase in the reaction system is propagated to the gaseous phase or the feed line of the gaseous feed system via the circulation line. Therefore, the flow rate of the gaseous reactant may be controlled through the use of the pressure fluctuation generated in relation to the pressure variation of the gaseous phase in the reaction system. For instance, the circulation flow rate of the gaseous reactant in the circulation line may be controlled based on the pressure fluctuation of the gaseous phase in the reaction system, and the feed flow rate of the gaseous reactant from the gas feed system may be controlled based on the pressure fluctuation of the gaseous phase in the gas feed system to supply the gaseous reactant to the reaction system via the feed line with the predetermined reference flow rate. Moreover, the apparatus of the present invention comprises a first pressure sensor for detecting the pressure of the gaseous phase in the reaction system; a first flow rate controlling unit for controlling the flow rate of the gaseous reactant in the circulation line in response to a detection signal from the first pressure sensor; a second pressure sensor for detecting the pressure fluctuation of the gaseous phase (of the feed unit or feed line) upstream side relative to the pressurizing means; and a second flow rate controlling unit for controlling the flow rate of the gaseous reactant in the feed line in response to a detection signal from the second pressure sensor.

The method of the present invention may be utilized for various reactions using a gaseous reactant, e.g., a carbonylation reaction. More specifically, the method comprises continuously supplying an alcohol to a liquid-phase pressurized reaction system containing a carbonylation catalytic system; supplying carbon monoxide to a compressor via a first feed line; continuously supplying carbon monoxide pressurized by the compressor to the reaction system via a second feed line with a reference flow rate F; and converging excess carbon monoxide in the reaction system in the first feed line via a circulation line branched from the second feed line for continuously producing a carboxylic acid by a carbonylation reaction in the reaction system; wherein carbon monoxide joined with the first feed line and the circulation line is continuously supplied to the reaction system via the second feed line with the reference flow rate F which is defined as the total rate of the reference consumption flow rate Fcs in the reaction system and the excess flow rate F1 in an excess amount over the fluctuation consumption flow rate ΔFcv in the reaction system, the flow rate of carbon monoxide of the circulation line is controlled to a total circulation rate Fr which is defined as the total rate of the excess flow rate F1 and a flow rate corresponding to the fluctuation consumption flow rate ΔFcv, in response to the pressure fluctuation of the gaseous phase of the reaction system, and the flow rate of carbon monoxide from the gas feed system to the first feed line is controlled to the total supply flow rate Fsu of the reference consumption flow rate Fcs and the flow rate corresponding to the fluctuation consumption flow rate ΔFcv, in response to the pressure fluctuation of the gaseous phase of the gas feed system, to adjust (or supplement) an excess or deficient amount of carbon monoxide relative to the reference flow rate F in the second feed line by carbon monoxide from the first feed line. In the method of the present invention, the reaction system may comprise a pressurized reaction system in which a carboxylic acid or a derivative thereof is produced by reaction of carbon monoxide with a $C_{1-4}$ alcohol or a derivative thereof, and for example, may comprise a liquid-phase pressurized reaction system for producing acetic acid or a derivative thereof by allowing methanol to react with carbon monoxide in a liquid phase in the presence of a carbonylation catalytic system.

The apparatus of the present invention includes an apparatus for the above-mentioned carbonylation reaction, for example, an apparatus which comprises a first feed line for supplying carbon monoxide to a compressor; a second feed line for continuously supplying carbon monoxide pressurized by the compressor to the pressurized reaction system; a circulation line branched from the second feed line for converging excess carbon monoxide in the reaction system in the first feed line, whereby carbon monoxide joined with the first feed line and the circulation line via the second feed line is continuously supplied to the reaction system with a reference flow rate F defined as the total rate of the reference consumption flow rate Fcs in the reaction system and an excess flow rate F1 in an excess amount over a fluctuation consumption flow rate $\Delta$Fcv in the reaction system; which further comprises a first pressure sensor for detecting the pressure of the gaseous phase in the reaction system; a first flow rate controlling unit for controlling the flow rate of carbon monoxide in the circulation line; a second pressure sensor for detecting the pressure in the first feed line; a second flow rate controlling unit for controlling the flow rate of carbon monoxide in the first feed line; a control unit for controlling the flow rate of carbon monoxide in the circulation line to a total circulation rate Fr defined as a total rate of the excess flow rate F1 and a flow rate corresponding to the fluctuation consumption flow rate $\Delta$Fcv by driving the first flow rate controlling unit in response to a detection signal from the first pressure sensor, and controlling the flow rate of carbon monoxide from the gas feed system to the first feed line to a total supply flow rate Fsu defined as the total rate of the reference consumption flow rate Fcs and the flow rate corresponding to the fluctuation consumption flow rate $\Delta$Fcv by driving the second flow rate controlling unit in response to a detection signal from the second pressure sensor, to adjust (or supplement) an excess or deficient amount of carbon monoxide relative to the reference flow rate F in the second feed line with carbon monoxide from the first feed line. In the apparatus, the feed unit for supplying carbon monoxide to the first feed line may comprise a purifying unit (column) for reserving (or storing) a liquid carbon monoxide; a second flow rate controlling unit for controlling the flow rate of the liquid carbon monoxide supplied from the purifying unit; a gasifying unit for producing gaseous carbon monoxide from the liquid carbon monoxide with a flow rate controlled by the flow rate controlling unit; a buffer tank for reserving gaseous carbon monoxide produced in the gasifying unit; and a second pressure sensor for detecting the pressure fluctuation of the buffer tank or the first feed line; and whereby, in response to a detection signal from the second pressure sensor, said controlling unit may control the flow rate of the liquid carbon monoxide by the second flow rate controlling unit for supplying an excess or deficient amount of carbon monoxide relative to the reference flow rate F in the second feed line.

Such a control apparatus is used for supplying a gaseous reactant (e.g., carbon monoxide) produced in a gaseous reactant-producing plant (e.g., a carbon monoxide-producing plant) to a pressurized reaction system of a compound-producing plant (e.g., a pressurized carbonylation reaction system of a carbonylation plant), wherein the control apparatus realizes to control the feed rate of the gaseous reactant (e.g., carbon monoxide) from the gaseous reactant-producing plant (e.g., the carbon monoxide-producing plant) based on the pressure fluctuation of the pressurized reaction system in the plant (e.g., the carbonylation reaction system). That is, in a system which unifies or unitizes management over operation of both plants, the fluctuation factors (such as a pressure fluctuation) in the reaction system may be reflected to controls of the producing plant (e.g., a carbon monoxide-producing plant) of the gaseous reactant and the feed system of the gaseous reactant (e.g., carbon monoxide), and the feed rate or amount of the gaseous reactant (e.g., carbon monoxide) may be controlled integrally or unitarily.

In such a method, the consumption flow rate Fc of the gaseous reactant in the reaction system may be represented by the total rate of the reference consumption flow rate Fcs which is steadily consumed by the reaction and the fluctuation consumption flow rate $\Delta$Fcv which fluctuates depending on varying the reaction temperature and other factors (i.e., Fc=Fcs+$\Delta$Fcv). To such a reaction system, the gaseous reactant is supplied with the reference flow rate F (F=Fcs+F1) represented by the total rate of the reference consumption flow rate Fcs and an excess flow rate F1 in an excess amount over the fluctuation consumption flow rate $\Delta$Fcv. Therefore, even if the consumption rate Fc of the gaseous reactant in the reaction system varies accompanied with the fluctuation consumption flow rate $\Delta$Fcv, the gaseous reactant can be supplied to the reaction system with the reference flow rate F having the excess flow rate F1 in an excess amount over the fluctuation consumption flow rate $\Delta$Fcv for ensuring a stable reaction. The circulation flow rate (return flow rate) Fr of the reactant in the circulation line may be represented by the difference (F1−$\Delta$Fcv) between the excess flow rate F1 and a flow rate corresponding to the fluctuation consumption flow rate $\Delta$Fcv. In the case where the pressure of a gaseous phase in the reaction system fluctuates with varying the consumption amount of the gaseous reactant, the feed (supply) flow rate or supplement (replenishment) flow rate of the gaseous reactant from the gas feed system is controlled to a predetermined flow rate Fsu (=Fcs+$\Delta$Fcv) in connection with the circulation flow rate Fr (=F1−$\Delta$Fcv) of the reactant in the circulation line, for supplying the gaseous reactant to the reaction system through the feed line with the predetermined reference flow rate F.

The meaning of the phrase "a pressure fluctuation of a gaseous phase in a reaction system" includes a pressure fluctuation not only of a gaseous phase in a reaction vessel but also of an area or field in which a pressure fluctuation of a gaseous phase in a reaction vessel is propagated (for example, an area communicated with the gaseous phase of the reaction vessel, such as a gas feed line extended to the reaction vessel). Accordingly, the fluctuation of the gaseous phase in the reaction system may be detected not only by a pressure sensor disposed at the feed line for supplying the gaseous reactant to the reaction vessel but also by a pressure sensor for directly measuring or detecting the pressure of the gaseous phase of the reaction vessel. The meaning of an area of "a pressure fluctuation of a gaseous phase in a gas feed system" includes a space for accommodating or reserving the gaseous reactant, or a flow passage for supplying the gaseous reactant (for example, the feed line extended from the gasifying system of a gaseous reactant to a pressurizing means).

DETAILED DESCRIPTION OF THE INVENTION

Figure 1:
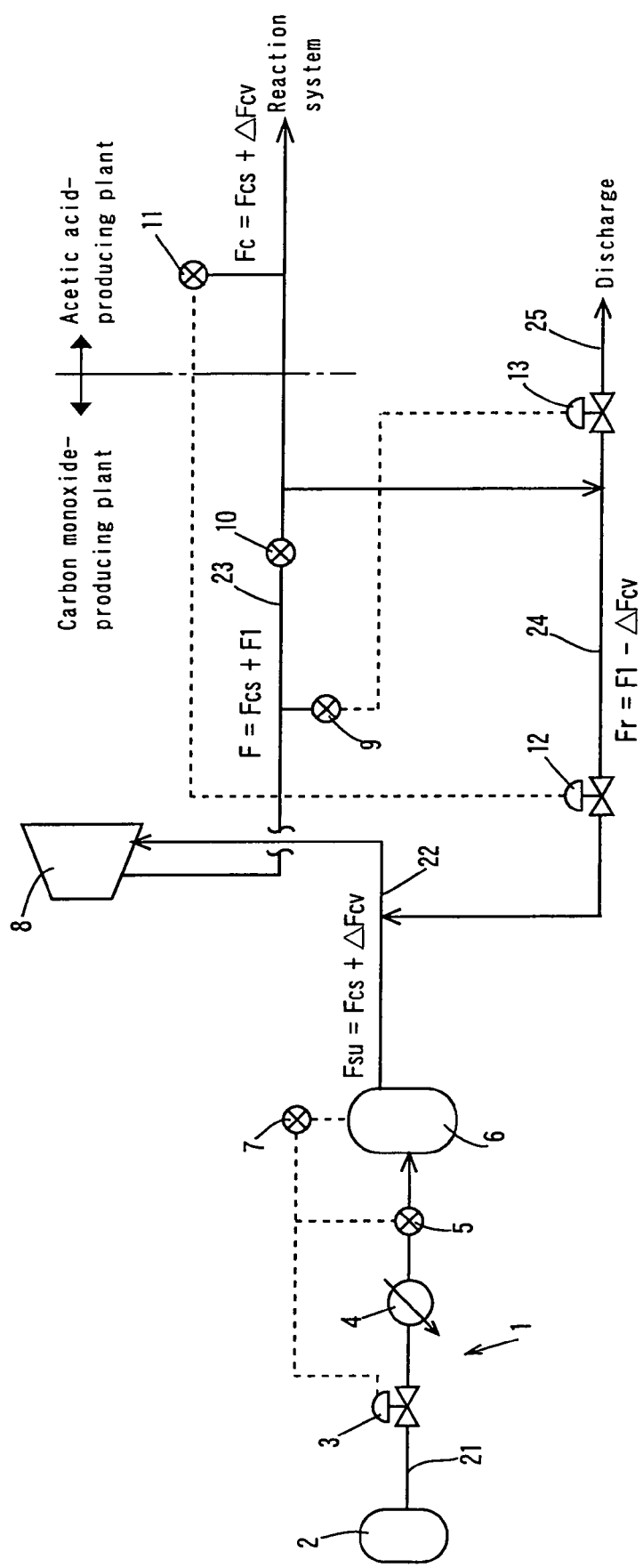
FIG. 1 shows a process flow diagram for illustrating a control method and control apparatus of the present invention.
Figure 2:
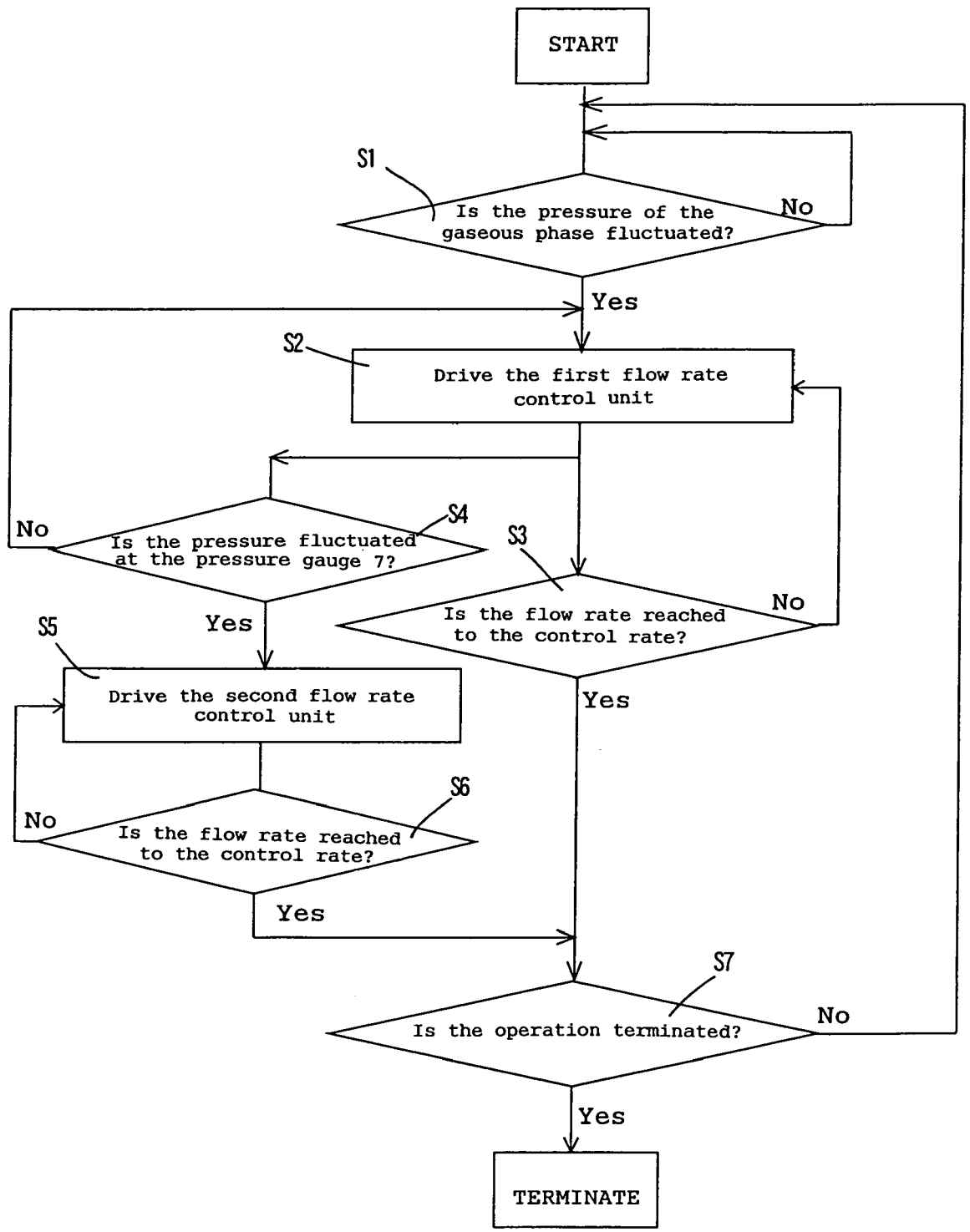
FIG. 2 shows a flow chart for illustrating an operation of the control apparatus of FIG. 1.

The present invention shall now be described in detail with reference if necessary to the attached drawings. FIG. 1 is a process flow diagram for illustrating a control method and control apparatus of the present invention, and FIG. 2 is a flow chart for illustrating the control apparatus of FIG. 1.

In this embodiment, a gaseous reactant (carbon monoxide) is continuously supplied from a producing plant for the gaseous reactant (for example, a carbon monoxide-producing plant) to a carbonylation plant (for example, an acetic acid-producing plant). That is, the embodiment illustrates a control process for supplying carbon monoxide from a carbon monoxide-producing plant to a reaction system (an acetic acid-producing plant for a liquid phase reaction system, not shown) for continuously producing a carboxylic acid (e.g., acetic acid) by a carbonylation reaction of an alcohol (e.g., methanol) with carbon monoxide (gaseous reactant) in the presence of a carbonylation catalytic system comprising a rhodium catalyst, lithium iodide, and methyl iodide. This control process controls the feed of carbon monoxide from the carbon monoxide-producing plant based on fluctuation factors (in particular, a pressure fluctuation) in the acetic acid-producing plant. In this process, an alcohol and a pressurized carbon monoxide are continuously supplied to a liquid-phase pressurized reaction system containing a carbonylation catalytic system, respectively.

The process comprises a feed unit (gas feed system) 1 for supplying or feeding carbon monoxide (gaseous reactant) from a gas feed source, a first feed line 22 for supplying carbon monoxide from the feed unit to a compressor 8, a second feed line 23 for continuously supplying carbon monoxide pressurized by the compressor 8, as a pressurizing means, to the reaction system (not shown), and a circulation line 24 branched from the second feed line and connected to the first feed line 22 for converging a surplus of carbon monoxide in the reaction system to the first feed line.

The feed unit (gas feed system) 1 comprises a purifying unit (purification column or gas feed source) 2 of a liquid carbon monoxide for reserving or storing the liquid carbon monoxide (liquefied carbon monoxide), a second flow rate controlling unit (such as an electromagnetic valve) 3 for controlling the flow rate of the liquefied carbon monoxide supplied from the purifying unit, and a gasifying unit (gas-producing unit) (such as a heat exchanger) 4 for producing gaseous carbon monoxide by vaporizing the liquid carbon monoxide at a flow rate controlled by the flow rate controlling unit 3. Carbon monoxide produced by the gasifying unit is supplied to a buffer tank 6, connected to the first feed line 22, for reserving or storing gaseous carbon monoxide. Incidentally, a vaporization line 21 extended from the purifying unit 2 to the buffer tank 6 is provided with the second flow rate controlling unit 3, the gasifying unit 4, and a flowmeter (or flow sensor) 5 for detecting a flow rate of gas produced by the gasifying unit, and a second pressure gauge (or pressure sensor) 7 for detecting an internal pressure of the buffer tank 6 is mounted on the buffer tank 6.

Carbon monoxide from the first feed line 22 is pressurized to a predetermined pressure by the compressor (gas pressurizing unit or compression unit) 8, and continuously supplied to the reaction system via the second feed line 23 with the reference flow rate F. Incidentally, the consumption flow rate Fc of carbon monoxide in the reaction system is defined as the total amount (Fc=Fcs+ΔFcv) of the reference consumption flow rate Fcs which is steadily consumed and the fluctuation consumption flow rate ΔFcv which is fluctuated depending on fluctuation factors (e.g., a temperature change). To ensure a stable reaction or operation in the case of varying the fluctuation consumption flow rate ΔFcv in the reaction system (acetic acid-producing plant), the reference flow rate F in the second feed line 23 is set as the total flow rate (F=Fcs+F1) of the reference consumption flow rate Fcs in the reaction system and an excess flow rate F1 (F1>ΔFcv) in an excess amount over the fluctuation consumption flow rate ΔFcv in the reaction system.

Further, the circulation line 24 is branched from the second feed line 23 and connected to the first feed line 22. A first pressure gauge (or pressure sensor) 11 for detecting the pressure of the gaseous phase in the pressurized liquid phase reaction system is mounted on the downstream side (acetic acid-producing plant side) of the second feed line 23 from the branched site of the circulation line 24. Furthermore, the circulation line 24 is provided with a first flow rate controlling unit (such as an electromagnetic valve) 12 for controlling the flow rate of carbon monoxide in the circulation line 24 in response to a detection signal from the first pressure gauge 11. That is, the pressure of the gaseous phase in the reaction system is in inverse proportion to the fluctuation consumption flow rate ΔFcv; when the fluctuation consumption flow rate ΔFcv has a negative value (Fc<Fcs: CO excess), the pressure is increased; and when the fluctuation consumption flow rate ΔFcv has a positive value (Fc>Fcs: CO deficiency), the pressure is decreased. To conduct the reaction under a predetermined pressure in the reaction system, the first flow rate controlling unit (such as an electromagnetic valve) 12 mounted on the circulation line 24 is controlled, in response to the detection signal from the first pressure gauge 11, for circulating an excess carbon monoxide in the reaction system to the first feed line 22 (then the reaction system) through the circulation line 24. The circulation flow rate Fr in the circulation line 24 may be represented by the difference (F1−ΔFcv) between the excess flow rate F1 and a flow rate corresponding to the fluctuation consumption flow rate ΔFcv.

The second feed line 23 is provided with a pressure gauge (pressure sensor) 9 for detecting a pressure of the second feed line, and a flowmeter (or flow sensor) 10 for detecting a flow rate of carbon monoxide. Further, a discharge line 25 is connected to the upstream side of the circulation line 24 relative to the first flow rate controlling unit 12. For taking measures to an emergency, the discharge line is provided with an emergency valve or electromagnetic valve 13 for releasing or discharging a gas in response to a detection signal from the pressure gauge 9 attached to the second feed line 23. That is, the emergency electromagnetic valve 13 is steadily shut, and when the detection signal from the pressure gauge 9 of the second feed line 23 reaches an abnormal level corresponding to unusual events (for example, remarkably increased pressure), the electromagnetic valve 13 is opened in response to the abnormal detection signal to discharge an excess gas from the discharge line 25.

In the first feed line 22, the flow rate of carbon monoxide from the feed unit 1 is controlled to maintain the feed rate of carbon monoxide in the second feed line 23 at the reference flow rate F in connection with the circulation flow rate in the circulation line 24. That is, in response to the detection signal from the first pressure gauge (pressure sensor) 11 for detecting the pressure of gaseous phase in the reaction system, the flow rate of carbon monoxide of the circulation line 24 is controlled to a total circulation rate Fr (=F1−ΔFcv, F1>ΔFcv) defined as the total flow rate of the excess flow rate F1 and a flow rate corresponding to the fluctuation consumption flow rate ΔFcv by driving the first flow rate controlling unit 12. In other words, in order to maintain the pressure of the reaction system at a reference pressure, opening and closing of the circulation line 24 is controlled by the first flow rate controlling unit 12 in relation to the pressure fluctuation relative to the reference pressure of the gaseous phase in the reaction system, for controlling the circulation flow rate of carbon monoxide to the circulation flow rate $Fr (=F1-\Delta Fcv, F1>\Delta Fcv)$ on the basis of the reference circulation flow rate $F1$ in the circulation line 24.

Further, the pressure fluctuation of the gaseous phase in the reaction system is also propagated to the first feed line 22 and the buffer tank 6 through the second feed line 23 and the circulation line 24. Thereby, the flow rate of the liquefied carbon monoxide is controlled by driving the second flow rate controlling unit (such as an electromagnetic valve) 3 of the feed unit 1 in response to the detection signal from the second pressure gauge 7 mounted on the buffer tank 6, for supplying carbon monoxide from the first feed line 22 with the total supply flow rate $Fsu (Fsu=Fcs+\Delta Fcv)$ which is the total flow rate of the reference consumption flow rate $Fcs$ and a flow rate corresponding to the fluctuation consumption flow rate $\Delta Fcv$. That is, an excess or deficient amount of carbon monoxide relative to the reference flow rate $F$ in the second feed line 23 is adjusted (or is made up for) with carbon monoxide from the first feed line 22, to permit convergence of the supplement flow rate in the first feed line 22 $(Fsu=Fcs=\Delta Fcv)$ and the circulation flow rate in the circulation line $(Fr=F1-\Delta Fcv)$, the converged carbon monoxide is supplied to the compressor 8 as the total flow rate $Fsu+Fr(=Fcs+F1=F)$, for controlling the flow rate of carbon monoxide in the second feed line 23 to the reference flow rate $F$.

The variation of the consumption rate of carbon monoxide (gaseous reactant) in the reaction system may be, accordingly, compensated or absorbed by the feed rate of carbon monoxide (gaseous reactant) from the gas feed system, and the reaction may be smoothly conducted with almost zero emission of carbon monoxide. Therefore, it is extremely advantageous industrially and economically in the respect that carbon monoxide is utilized for the reaction with almost 100% rate and that acetic acid is stably and continuously produced. Moreover, the feed rate of carbon monoxide to the compressor 8 can be maintained at an almost constant rate, and the load fluctuation to the compressor 8 can be reduced to inhibit effectively the occurrence of surging. Further, since the liquefied carbon monoxide is used as a gas feed source in the feed unit 1, a controlled system (the liquefied carbon monoxide) can be precisely controlled by the second flow rate controlling unit 3 with a predetermined controlled variable. Moreover, since, by use of the liquefied carbon monoxide, the reservoir capacity can be downsized and the fluctuation $\Delta Fcv$ of the consumption rate of carbon monoxide can be compensated by the slight fluctuation of the liquid level (or a small amount to be taken out) in the carbon monoxide-purifying unit (purification column) 2 in comparison with the fluctuation of the feed rate of gaseous carbon monoxide, the apparatus can be downsized, and as a result, it is unnecessary to use a large scale equipment.

In such a control method or control apparatus, the detection signal from the pressure gauge 11 for detecting the pressure of the gaseous phase in the reaction system is fed to the first control unit. The control unit comprises a memory circuit (or setting circuit) for storing a reference value (threshold) with respect to the reference pressure of the gaseous phase in the reaction system, a comparison unit (comparison circuit) for comparing the reference value (threshold) of the memory circuit with a detection signal level from the pressure gauge 11, an arithmetic (or operation) unit (arithmetic circuit) for calculating a controlled variable with respect to the flow rate of carbon monoxide based on the deviation between the reference value and the detection signal level, when the comparison unit finds that the detection signal level is deviated from the reference value, and a driving or actuating unit (driving circuit) for driving the first flow rate controlling unit 12 of the circulation line 24 based on the controlled variable calculated by the arithmetic unit.

Moreover, the detection signal from the second pressure gauge 7 for detecting the pressure of the buffer tank 6 is fed to the second control unit. The control unit comprises a memory circuit (or setting circuit) for storing a reference value (threshold) with respect to the reference pressure in the first feed line 22, a comparison unit (comparison circuit) for comparing the reference value (threshold) of the memory circuit with a detection signal level from the second pressure gauge 7, an arithmetic (or operation) unit (arithmetic circuit) for calculating or computing a controlled variable with respect to the supplement flow rate of carbon monoxide based on the deviation between the reference value and the detection signal level when the comparison unit finds that the detection signal level is deviated from the reference value, and a driving or actuating unit (driving circuit) for driving the second flow rate controlling unit 3 attached to the vaporization line 21 based on the controlled variable calculated by the arithmetic unit.

As shown in FIG. 2, when the control unit (or control apparatus) is driven in response to a start signal, in step S1, it is discriminated whether or not the pressure of the gaseous phase in the reaction system is varied based on the detection signal from the first pressure gauge 11 and the reference value (threshold) with respect to the reference pressure of the memory circuit. When the detection signal level is deviated from the reference value (threshold) by pressure fluctuations, the first flow rate controlling unit is driven and controlled in step S2 based on the controlled variable calculated by the arithmetic circuit, and it is discriminated whether or not the driving rate (or amount) reaches the controlled variable $(Fr=F1-\Delta Fcv)$ in step S3. Moreover, when the first flow rate controlling unit is driven in step S2, it is discriminated in step 4 whether or not the pressure of the gaseous phase in the buffer tank 6 is varied based on the detection signal from the second pressure gauge 7 and the reference value (threshold) with respect to the reference pressure of the memory circuit. When the detection signal level is deviated from the reference value (threshold) by pressure fluctuations, the second flow rate controlling unit is driven and controlled in step S5 based on the controlled variable calculated by the arithmetic circuit, and it is discriminated whether or not the driving rate (or amount) reaches the controlled variable $(Fsu=Fcs+\Delta Fcv)$ in step S6.

In the case where the driving rate does not reach the controlled variable in steps S3 and S6, the driving of the controlling units is further continued. The reach of the driving rate to the controlled variable in steps S3 and S6 stops the operations of the drive control, and, in step 7, it is discriminated whether or not the operation should be stopped (that is, whether or not the flow rate control by the control apparatus should be terminated). In the case where the flow rate control will not be terminated, it is discriminated whether the pressure of the gaseous phase is fluctuated by returning to step S1.

The necessity of the termination of the flow rate control in step S7 may be determined on the basis whether or not the flow rate reaches a reference value regarding a time base (such as an accumulated operation time) or a reference value with respect to a flow rate base (such as an accumulated flow rate by the flow rate 10) as an index.

Incidentally, in the present invention, the feed line may comprise a plurality of feed lines, and the flow rate of a gaseous reactant may be controlled by at least one feed line. For example, the feed line may comprise a line for supplying a gaseous reactant to a reaction system with a reference consumption flow rate, and a line for supplying a gaseous reactant with a fluctuation consumption flow rate (an exclusive feed line for the fluctuation consumption rate). Moreover, the compressor (pressurizing means) may also comprise a plurality of compressors disposed in a serial and/or parallel arrangement. Further, the circulation line may also comprise a plurality of lines, and the flow rate may be controlled by at least one circulation line. Moreover, the circulation line may be branched from a feed line (in particular a second feed line) for supplying a gaseous reactant to a reaction vessel, and if necessary may be connected to a reaction vessel through a condenser or others.

The flow rate control may be conducted based on (or in reference to) a pressure fluctuation of a gaseous phase in a reaction system by utilizing the correlation between a pressure fluctuation and a consumption rate of a gaseous reactant, and the feed rate of the gaseous reactant from the gas feed system may be controlled in connection with the circulation flow rate of the gaseous reactant in the circulation line for realizing the feed of the gaseous reactant to the reaction system through the feed line with a predetermined reference flow rate. More specifically, in order to compensate or absorb the consumption rate fluctuation of the gaseous reactant in the reaction system by the feed rate of the gaseous reactant from the gas feed system for realizing a substantial zero discharge of the gaseous reactant, as described above, it is advantageous to control the flow rate of the gaseous reactant in the circulation line and that of the gaseous reactant from the feed unit to the feed line, respectively, in association or connection with the fluctuation consumption rate of the gaseous reactant by the controlling unit (or controlling apparatus) for continuously supplying a converged gaseous reactant from the feed line and the circulation line to the reaction system with a reference flow rate F which is determined as the total flow rate of the reference consumption flow rate Fcs in the reaction system and an excess flow rate F1 in an excess amount relative to the fluctuation consumption flow rate $\Delta$Fcv in the reaction system. The reference flow rate F has only a surplus or excess rate F1 over the reference consumption flow rate Fcs as mentioned above, and the reactant of the consumption flow rate Fc is consumed with accompanying by the reference consumption flow rate Fcs and the fluctuation consumption flow rate $\Delta$Fcv (F1>$\Delta$Fcv).

Incidentally, the control flow for the flow rate is not limited to the specific above embodiments, and various control flows may be used. For example, it is unnecessary to operate in parallel the driving or controlling operations of the controlling unit in step S2 and step S5 with discriminant operations in step S3 and step S6. The control flow may comprise, e.g., a control flow for controlling the circulation flow rate of the circulation line by controlling the first flow rate controlling unit 12 based on the detection signal from the first pressure gauge 11, and a control flow for controlling the flow rate in the first feed line by controlling the second flow rate unit 3 based on the detection signal from the second pressure gauge 7, independently of the detection signal from the first pressure gauge 11. These independent control systems may control each flow rate concurrently or in parallel.

Moreover, the second flow rate controlling unit may be controlled by controlling the first flow rate controlling unit in response to the detection signal from the first pressure gauge, and by discriminating or comparative detecting whether the pressure fluctuation is caused or not on the basis of the detection signal from the second pressure gauge in response to the detection signal from the first pressure gauge.

Further, the pressure fluctuation of the gaseous phase in the reaction system is propagated to the buffer tank 6, and there is a correlation between the detection signal from the first pressure gauge 11 (or pressure fluctuation of the reaction system) and the controlled variable by the second flow rate controlling unit 3. According to the present invention, the first flow rate controlling unit 12 and the second flow rate controlling unit 3 may be controlled in relation to the pressure fluctuation of the gaseous phase in the reaction system (that is, with reference to the detection signal from the first pressure gauge 11) without utilizing the detection signal from the second pressure gauge 7. In other words, the flow rate control may be conducted by the steps of; detecting the pressure of the gaseous phase in the reaction system with at least the first pressure sensor, and controlling the flow rate of the feed line and that of the circulation line with the controlling unit in response to the detection signal from the first pressure sensor. Moreover, in the case where the flow rate of the feed line and that of the circulation line are controlled with the use of the first pressure sensor, the control by the second flow rate controlling unit may be conducted by driving with a predetermined decay time constant (predetermined time delay) from the start for driving the first flow rate controlling unit in consideration of the arrival time or other factors of the gaseous reactant from the circulation line to the feed line.

The preferred method or apparatus of the present invention comprises a first pressure sensor for detecting the pressure of the gaseous phase in the reaction system, a first flow rate controlling unit for controlling or regulating the flow rate of the gaseous reactant in the circulation line, a second pressure sensor for detecting the pressure fluctuation of the gaseous phase upstream side relative to the pressurizing means attached to the feed line (a gaseous phase of a space communicated with the circulation line, for example a gaseous phase of the feed unit or the first feed line), and a second flow rate controlling unit for controlling or regulating the flow rate of the gaseous reactant in the first feed line in response to the detection signal from the second pressure sensor. Further, the method or apparatus comprises a controlling unit for controlling the flow rates by the first and second flow rate-controlling units in response to the detection signals from the first and second pressure sensors. The control unit drives or actuates the first flow rate controlling unit for controlling the flow rate of carbon monoxide of the circulation line to a total circulation rate Fr which is a total flow rate of the excess flow rate F1 and a flow rate corresponding to the fluctuation consumption flow rate $\Delta$Fcv, and drives or actuates the second flow rate controlling unit for controlling the flow rate of carbon monoxide from the gas feed system to the first feed line to the total supply flow rate Fsu which corresponds to the total flow rate of the reference consumption flow rate Fcs and the flow rate corresponding to the fluctuation consumption flow rate $\Delta$Fcv. Such a control unit insures effective adjustment or supplement of an excess or deficient amount of carbon monoxide relative to the reference flow rate F in the second feed line, with the use of carbon monoxide from the first feed line.

The pressure fluctuation of the gaseous phase in the gas feed system may be practically detected in a feed system for supplying the gaseous reactant supplied from the gas feed source to the pressurizing means (in particular a passage from the buffer tank to the pressurizing means). For example, the pressure fluctuation may be detectable by a pressure gauge not only mounted on the buffer tank but also attached to a suitable position of the first feed line.

The gas feed source may not be limited to the liquefied gas, and may be a vaporized gas. Use of the liquid (or liquefied reactant) insures to reduce remarkably the controlled variable in volume and realizes a precise flow rate control because the source is in a liquid form. Moreover, the liquefied reactant ensures to compact a reserve volume compared with the gaseous carbon monoxide, and to supplement for the fluctuated gas consumption rate confronted by a small amount of supply. That is, the fluctuation of the gas consumption rate can be compensated with a slight fluctuation of the liquid level in the carbon monoxide-purifying unit (purifying column) so that no large-scale equipment is required. Accordingly, by utilizing the control unit, the flow rate of the liquefied reactant by the second flow rate controlling unit (furthermore the height of the liquid level in the purifying column) can be controlled to the supplement flow rate Fsu as a vaporized gaseous reactant with high precision, in response to the detection signal from the pressure sensor, to supply a compensated amount of carbon monoxide for an excess or deficient amount of carbon monoxide relative to the reference flow rate F in the second feed line.

With respect to the flow control, various process control modes or forms such as a feedback control may be used for control of the flow rate, and examples of such process control actions include a proportional control action (P control action), with which the manipulated variable is controlled in proportion to the deviation of the flow rate from the reference flow rate, an integral control action (I control action), with which the manipulated variable is controlled by or upon integrating the flow rate deviation, a differential control action (D control action), with which the manipulated variable is controlled in accordance with the variation of the flow rate deviation, actions in which the above actions are combined (for example, a PI action, a PD action, and a PID action). For example, in accordance with the I action, a deviation of the flow rate with respect to the reference flow rate may be integrated respectively over a predetermined period of time in each feed line and a circulation line, and the flow rate of the gaseous reactant in each line may be controlled when the integrated amount of the flow rate deviation reaches a predetermined flow rate.

The fluctuation consumption flow rate $\Delta Fcv$ in a pressurized reaction system (in particular a liquid-phase pressurized reaction system) changes significantly depending on various fluctuation factors (for example, the temperature fluctuation in the reaction system, and the amount of a catalyst). In particular, in an industrial manufacturing plant, a slight change of the reaction temperature results in a large amount of emission (or discharge) of a gaseous reactant (such as carbon monoxide). Even in such a reaction system, the present invention realizes an industrially advantageous reaction system with accomplishing a substantial zero emission of the gaseous reactant.

The present invention may be applied to a variety of processes which comprise continuously supplying a gaseous reactant from a gas feed system to a pressurized reaction system through a feed line and circulating a surplus (or excess) gaseous reactant in the reaction system from the feed line to the reaction system through a circulation line. The reaction of the process includes, for example, a carbonylation reaction using carbon monoxide, an oxidative reaction using a gaseous oxidant (such as oxygen or ozone), a hydrogen reduction reaction, and various other reactions using a gaseous reactant [e.g., carbon dioxide, a nitrogen oxide, a sulfur oxide (such as sulfur dioxide), a halogen, or a halide]. The reactant may be selected depending on the type of reaction, and is not particularly limited to a specific one. For instance, examples of components used for the carbonylation reaction include a combination of carbon monoxide and an alcohol (e.g., a $C_{1-10}$alkyl alcohol such as methanol) or a derivative thereof (e.g., a carboxylic acid ester such as methyl acetate, a $C_{1-10}$alkyl iodide such as methyl iodide, a $diC_{1-6}$alkyl ether such as methyl ether) [for production of a carboxylic acid (such as acetic acid) or a derivative thereof]; a combination of carbon monoxide, an olefin (e.g., ethylene, propylene, butene, allene), and hydrogen [for production of an aldehyde (such as acetaldehyde)]; a combination of carbon monoxide, the olefin, and water (for production of a carboxylic acid); a combination of carbon monoxide, the olefin, and the alcohol (for production of a carboxylic acid ester); a combination of carbon monoxide, an alkyne (e.g., acetylene, methyl acetylene), and water [for production of an unsaturated carboxylic acid (such as acrylic acid, methacrylic acid)]; a combination of carbon monoxide, the alkyne, and the alcohol (e.g., methanol) [for production of an unsaturated carboxylic acid ester (such as methyl acrylate, methyl methacrylate)]; a combination of carbon monoxide, the alcohol, and oxygen (for production of a diester carbonate); and others.

The preferred pressurized reaction system includes a reaction system for obtaining a carboxylic acid or a derivative thereof (e.g., a carboxylic anhydride) by using carbon monoxide, and an alcohol, as a liquid reactant, preferably a $C_{1-4}$ alcohol or a derivative thereof (e.g., methanol, methyl acetate, methyl iodide, and diethyl ether), in particular, a liquid-phase pressurized reaction system for producing acetic acid or a derivative thereof by allowing to react methanol with carbon monoxide in the presence of a carbonylation catalytic system in a liquid phase reaction system.

The above-mentioned carbonylation catalyst may be selected depending on the type of carbonylation reaction. The carbonylation catalyst includes, for example, a transition metal-series catalyst such as a rhodium catalyst, an iridium catalyst, a platinum catalyst, a palladium catalyst, a copper catalyst, a nickel catalyst and a cobalt catalyst. The carbonylation catalyst may be used as a catalyst system by combining a co-catalyst or accelerator such as an alkali metal halide (e.g., lithium iodide), a hydrogen halide (e.g., hydrogen iodide) and an alkyl halide (e.g., methyl iodide). Moreover, for the production of (meth)acrylic acid or an ester thereof, etc., an amine (e.g., a chain or cyclic tertiary amine) or an organic sulfonic acid (e.g., an alkyl sulfonic acid such as methanesulfonic acid or a salt thereof) may be used as a co-catalyst or accelerator.

The carbon monoxide may be used as a pure gas or may be used with diluting by an inert gas (for example, nitrogen, helium, and carbon dioxide). The partial pressure of carbon monoxide in the reaction system may be selected suitably according to the type or mode of reaction, etc. For example, for the production of a carboxylic acid by a carbonylation reaction of an alcohol, the partial pressure of carbon monoxide in the reaction system is, for example, about 200 to 3000 kPa, preferably about 400 to 1500 kPa, and more preferably about 500 to 1000 kPa.

In the carbonylation reaction system equipped with the pressurized reaction system, the reaction pressure and temperature may be selected suitably according to the type or mode of reaction, and the reaction pressure may, for example, be about 1000 to 5000 kPa (e.g., about 1500 to 4000 kPa), and the reaction temperature may, for example, be about 100 to 250° C. (preferably about 150 to 220° C., and more preferably about 170 to 200° C.).

According to the present invention, the fluctuation of the consumption rate of the gaseous reactant in a reaction system can be compensated or absorbed by the feed rate of the gaseous reactant from a gas feed system to insure effective utilization of the gaseous reactant (such as carbon monoxide) for a reaction in a pressurized reaction system. In particular, even in a pressurized reaction system in which an excess flow rate of the gaseous reactant is fed, discharge or release of the gaseous reactant can be suppressed to zero emission substantially, resulting in economically advantageous reaction of the gaseous reactant. Further, in an industrial pressurized reaction system (e.g., a carbonylation reaction system) in which an excess amount of a gaseous reactant over a reference flow rate is continuously supplied to a reaction system, the gaseous reactant can be effectively utilized for the reaction even when the consumption amount of carbon monoxide fluctuates in the reaction system. Furthermore, based on fluctuation factors in a carbonylation plant (e.g., an acetic acid-producing plant), the present invention insures control of a feed rate of a gaseous reactant in a producing plant of the gaseous reactant and realizes a unitary management for the carbonylation plant and the producing plant of the gaseous reactant.

INDUSTRIAL APPLICABILITY

The present invention is preferably applicable to various processes or plants using a gaseous reactant, for instance, a process or plant for producing a carboxylic acid or a derivative thereof by utilizing a carbonylation reaction.

EXAMPLES

The following examples are intended to describe this invention in further detail and should by no means be construed as defining the scope of the invention.

Comparative Example

Figure 3:
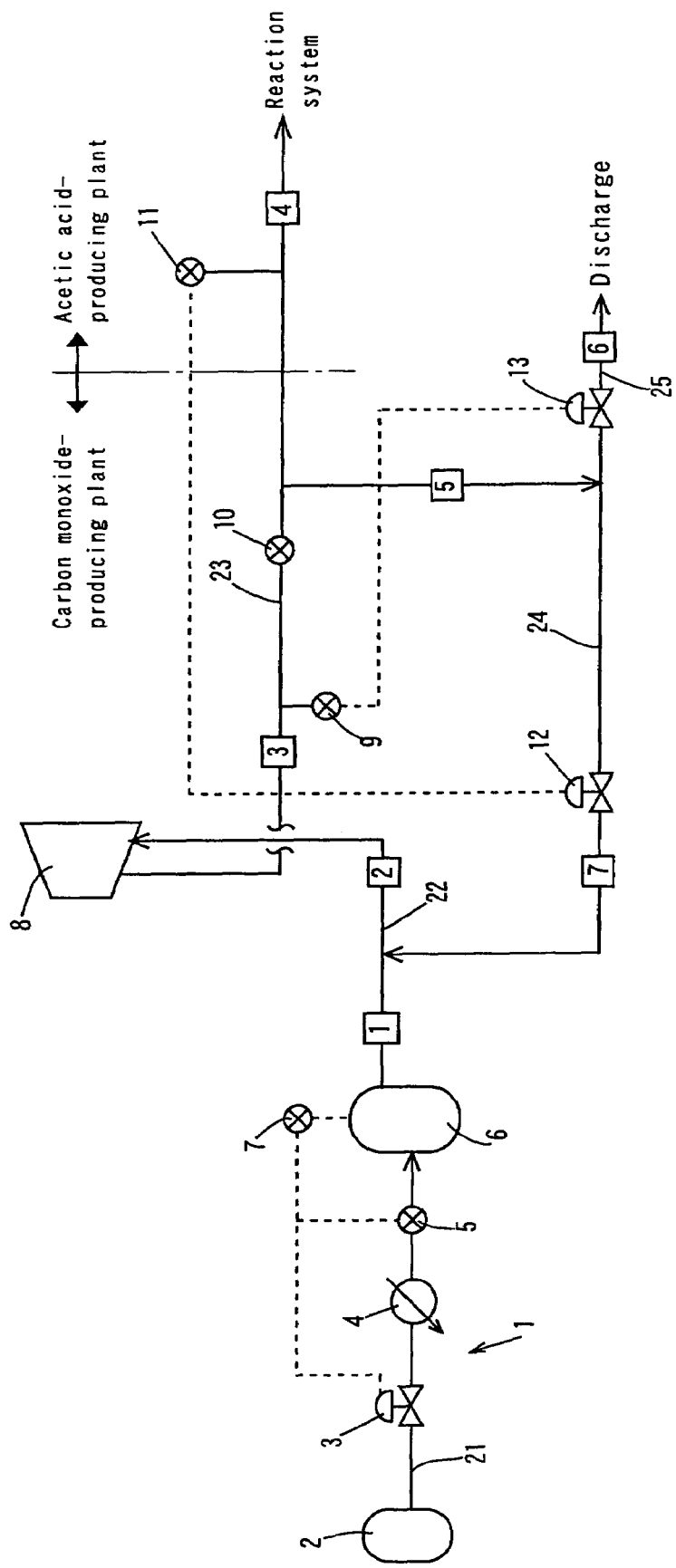
FIG. 3 shows a process flow diagram for explaining an Example and Comparative Example.

In the process flow of FIG. 3 in relation to FIG. 1, the flow rate and pressure in a system for feeding carbon monoxide to an acetic acid production process were measured with both of flowmeters and pressure gauges, respectively, attached or installed to the following lines:

(1) a vaporization line 21,
(2) a downstream side of a first feed line 22 from a juncture site with a circulation line 24,
(3) an upstream side of a second feed line 23 from a branched site of the circulation line 24,
(4) a downstream side of the second feed line 23 from a branched site of the circulation line 24,
(5) an upstream side of the circulation line 24 from a junction site with a discharge line 25,
(6) the discharge line 25, and
(7) a downstream side of the circulation line 24 from a junction site with the discharge line 25.

A carbonylation reaction in a liquid phase reaction system was conducted under a reference partial pressure of carbon monoxide of 700 to 755 kPa, a reference pressure of 2775 kPa, and a reference temperature of 187.5° C. by supplying a pressurized carbon monoxide of 3236 kPa pressurized by the compressor to the reaction vessel with supplying carbon monoxide from the first feed line with a pressure of 294 kPa, and supplying methanol to the reaction vessel with a flow rate of 29 kg/H (kg/hour). The reaction was conducted in a rhodium iodide concentration of 550 to 600 ppm, a methyl iodide concentration of 12 to 13% by weight, a lithium iodide concentration of 4.7 to 4.9% by weight, a methyl acetate concentration of 1.5 to 1.7% by weight, and a water concentration of 7.8 to 8.0% by weight in the liquid phase. Moreover, part of the resulting reaction product was supplied to a flash distillation column with continuously taking out from the reaction vessel, and a high boiling component separated by the flash distillation column (containing a catalyst, etc.) was returned to the reaction vessel. Further, a low boiling component separated by the flash distillation column was supplied to a purification column, and a low boiling component separated by the purification column (containing methyl iodide, etc.) was returned to the reaction vessel.

With respect to the flow rate control, in order to maintain the pressure of the second feed line to be approximately constant pressure (3236 kPa) by supplying a carbon monoxide flow from the first feed line at a constant flow rate (21.8 Nm³/H), the pressure fluctuation of the gaseous phase in the reaction system was detected by the pressure gauge 9, and the flow rate control valve 13 of the discharge line 25 was driven in response to the detection signal with retaining or maintaining the flow rate at 23 Nm³/H based on a signal from the flowmeter 10, and the excess amount of carbon monoxide was combusted with discharging from the discharge line 25.

Example

In the process flow shown in FIG. 3, the reaction was conducted in the same manner as in the Comparative Example except that the amount or rate of carbon monoxide corresponding to the pressure fluctuation of the gaseous phase in the reaction vessel was supplemented by the following procedures. The pressure fluctuation of the gaseous phase in the reaction system was detected with the pressure gauge 11, the first flow rate controlling unit 12 was driven in response to the detection signal for controlling the circulation flow rate in the circulation line to a flow rate (Fr=F1−ΔFcv), the pressure fluctuation of the inlet side of the compressor 8 was detected with the pressure sensor 7 mounted on the buffer tank 6, and the second flow rate controlling unit 3 was driven in response to the detection signal to control the feed flow rate of carbon monoxide from the first feed line to a flow rate (Fsu=Fcs+ΔFcv). For reducing the load fluctuation to the compressor, the pressure of carbon monoxide joined in the circulation line and the first feed line was set up to an approximately constant pressure of 294 kPa. Moreover, in the case where an abnormal or unusual pressure was detected by the pressure gauge 9 installed to the second feed line, the flow rate control valve 13 attached to the discharge line 25 was driven for combusting the excess amount of carbon monoxide with discharging from the discharge line 25.

The results are shown in Table 1. Concerning the flow rate of carbon monoxide, the flow rate of carbon monoxide in each line is represented by assuming that the flow rate of carbon monoxide supplied from the first feed line of the carbon monoxide-producing plant is "100".

TABLE 1

| | | Comparative Example | Example |
|---|---|---|---|
| Vaporization line (1) | Flow rate | 100 | 98.6 to 101.4 |
| | Pressure (kPa) | 294 | 294 |
| First feed line (2) | Flow rate | 105.5 | 105.5 |
| | Pressure (kPa) | 294 | 294 |
| Second feed line (3) | Flow rate | 105.5 | 105.5 |
| | Pressure (kPa) | 3236 | 3236 |
| Second feed line (4) | Flow rate | 97.2 to 100 | 98.6 to 101.4 |
| | Pressure (kPa) | 3138 | 3138 |
| Circulation line (5) | Flow rate | 5.5 to 8.3 | 4.1 to 6.9 |
| | Pressure (kPa) | 3236 | 3236 |
| Discharge line (6) | Flow rate | 0 to 2.8 | 0 |
| | Pressure (kPa) | — | — |
| Circulation line (7) | Flow rate | 5.5 | 4.1 to 6.9 |
| | Pressure (kPa) | 294 | 294 |

Compared with the above-mentioned Comparative Example, the method of Example positively reduces the carbon monoxide discharge to substantially zero by controlling the flow rate of the first feed line and that of the circulation line in response to the pressure fluctuation of the reaction system to permit effective utilization of carbon monoxide for the carbonylation reaction.

The invention claimed is:

1. A method of controlling a gaseous reactant which comprises:
   supplying a gaseous reactant from a gas feed system to a compressor via a first feed line,
   continuously supplying the gaseous reactant pressurized by the compressor to a pressurized reaction system via a second feed line, and
   circulating or returning an amount of the gaseous reactant corresponding to an amount in excess in the reaction system from the second feed line to the first feed line via a circulation line that branches from the second feed line, to join the circulated gaseous reactant with the gaseous reactant in the first feed line at a junction of the first feed line and the circulation line,
   wherein a circulation flow rate of the gaseous reactant in the circulation line and a feed flow rate of the gaseous reactant from the gas feed system to the first feed line are controlled based on the pressure fluctuation of a gaseous phase in the reaction system, and the gaseous reactant comprises carbon monoxide and the reaction system is a carbonylation reaction system.

2. The method according to claim 1, wherein the gaseous reactant joined at the junction of the first feed line and the circulation line is continuously supplied to the second feed line with a reference flow rate F which is defined as the total flow rate of a reference consumption flow rate Fcs in the reaction system and an excess flow rate F1 in an excess amount over a fluctuation consumption flow rate ΔFcv in the reaction system.

3. The method according to claim 1, wherein the gas feed source of the gas feed system is in a liquid form, and a consumption rate fluctuation of the gaseous reactant in the reaction system is compensated or absorbed by a feed rate of the gaseous reactant from the gas feed system.

4. The method according to claim 1, wherein the circulation flow rate of the gaseous reactant in the circulation line is controlled based on the pressure fluctuation of the gaseous phase in the reaction system, and the feed flow rate of the gaseous reactant from the gas feed system is controlled based on the pressure fluctuation of the gaseous phase in the gas feed system to supply the gaseous reactant to the reaction system via the first feed line with a predetermined reference flow rate.

5. The method according to claim 1, further comprising:
   continuously supplying an alcohol to a liquid-phase pressurized carbonylation reaction system containing a carbonylation catalytic system,
   supplying carbon monoxide to the compressor via the first feed line,
   continuously supplying carbon monoxide pressurized by the compressor to the second feed line with a reference flow rate F, and
   joining (a) an amount of carbon monoxide corresponding to an amount excess in the reaction system returned from the second feed line via a circulation line branched from the second feed line with (b) the carbon monoxide in the first feed line for continuously producing a carboxylic acid by a carbonylation reaction in the reaction system,
   wherein carbon monoxide joined at the junction of the first feed line and the circulation line is continuously supplied to the second feed line with the reference flow rate F which is defined as the total rate of a reference consumption flow rate Fcs in the reaction system and the excess flow rate F1 in an excess amount over a fluctuation consumption flow rate ΔFcv in the reaction system, the flow rate of carbon monoxide of the circulation line is controlled to a total circulation rate Fr which is defined as the total rate of the excess flow rate F1 and a flow rate corresponding to the fluctuation consumption flow rate ΔFcv, in response to the pressure fluctuation of the gaseous phase of the reaction system, the flow rate of carbon monoxide from the gas feed system to the first feed line is controlled to the total supply flow rate Fsu of the reference consumption flow rate Fcs and the flow rate corresponding to the fluctuation consumption flow rate ΔFcv, in response to the pressure fluctuation of the gaseous phase of the gas feed system, to adjust an excess or deficient amount of carbon monoxide relative to the reference flow rate F by carbon monoxide from the gas feed system.

6. The method according to claim 1, wherein the reaction system comprises a pressurized reaction system in which a carboxylic acid or a derivative thereof is produced by a reaction of carbon monoxide with a $C_{1-4}$ alcohol or a derivative thereof.

7. The method according to claim 1, wherein the reaction system comprises a liquid-phase pressurized reaction system for producing acetic acid or a derivative thereof by allowing methanol to react with carbon monoxide in a liquid phase in the presence of a carbonylation catalytic system.

* * * * *